US006669929B1

(12) United States Patent
Boyd et al.

(10) Patent No.: US 6,669,929 B1
(45) Date of Patent: Dec. 30, 2003

(54) DENTIFRICE CONTAINING FUNCTIONAL FILM FLAKES

(75) Inventors: Thomas J. Boyd, Somerset, NJ (US); Guofeng Xu, Princeton, NY (US); M. Teresa R. Carale, Princeton, NY (US)

(73) Assignee: Colgate Palmolive Company, New York, NY (US)

( * ) Notice: Subject to any disclaimer, the term of this patent is extended or adjusted under 35 U.S.C. 154(b) by 0 days.

(21) Appl. No.: 10/331,312

(22) Filed: Dec. 30, 2002

(51) Int. Cl.$^7$ ................................................. A61K 7/16
(52) U.S. Cl. ........................................................ 424/49
(58) Field of Search ...................... 427/49–58

(56) References Cited

U.S. PATENT DOCUMENTS

| | | | | |
|---|---|---|---|---|
| 919,736 A | * | 4/1909 | Loesch | |
| 1,429,405 A | * | 9/1922 | Carter et al. | |
| 1,605,903 A | * | 11/1926 | Schuler | |
| 1,785,078 A | * | 12/1930 | Gibson | |
| 1,947,124 A | * | 2/1934 | Clauss | 53/10 |
| 2,062,867 A | * | 12/1936 | Cosler | 107/54 |
| 2,137,170 A | * | 11/1938 | Levey | 127/29 |
| 2,353,594 A | * | 7/1944 | Seagron | 41/33 |
| 2,394,322 A | * | 2/1946 | McKee | 99/92 |
| 2,526,811 A | * | 10/1950 | Dawson | 107/20 |
| 2,610,588 A | * | 9/1952 | Seagren et al. | 107/7 |
| 2,624,277 A | * | 1/1953 | Sunkoz | 101/129 |
| 2,645,049 A | * | 7/1953 | Brown | 41/24 |
| 2,791,960 A | * | 5/1957 | Pietropinto | 99/430 |
| 2,846,314 A | * | 8/1958 | Aichele et al. | 99/139 |
| 2,895,832 A | * | 7/1959 | Bersey | 99/92 |
| 3,009,812 A | * | 11/1961 | Ganz | 99/139 |
| 3,711,604 A | * | 1/1973 | Cologney et al. | 424/52 |
| 3,852,494 A | * | 12/1974 | Williamson | 426/383 |
| 3,934,000 A | * | 1/1976 | Barth | 424/47 |
| 3,944,661 A | * | 3/1976 | Colodney et al. | 424/49 |
| 3,954,961 A | * | 5/1976 | Colodney et al. | 424/49 |
| 3,957,968 A | * | 5/1976 | Cordon | 424/57 |
| 4,075,316 A | * | 2/1978 | Cordon | 424/49 |
| 4,285,978 A | * | 8/1981 | Quinlivan | 426/87 |
| 4,650,685 A | * | 3/1987 | Persson et al. | 426/285 |
| 4,849,212 A | * | 7/1989 | Glandorf et al. | 424/52 |
| 4,956,404 A | * | 9/1990 | Pelzig | 524/48 |
| 5,017,394 A | * | 5/1991 | Macpherson et al. | 426/302 |
| 5,035,906 A | * | 7/1991 | Persson et al. | 426/285 |
| 5,447,584 A | * | 9/1995 | Shakespeare et al. | 156/63 |
| 5,643,603 A | * | 7/1997 | Bottenberg et al. | 424/488 |
| 5,869,029 A | * | 2/1999 | Graff-Andersen et al. | 424/52 |
| 5,931,999 A | * | 8/1999 | Aisner | 106/436 |
| 5,958,525 A | * | 9/1999 | Green et al. | 428/14 |
| 5,990,205 A | * | 11/1999 | Cordova | 524/55 |
| 6,051,059 A | * | 4/2000 | Aisner | 106/436 |
| 6,251,452 B1 | * | 6/2001 | Weinstein et al. | 426/249 |
| 6,258,342 B1 | * | 7/2001 | Harcum et al. | 424/49 |
| 6,497,899 B2 | * | 12/2002 | Thombre et al. | 424/464 |
| 6,586,013 B2 | * | 7/2003 | Victor | |

FOREIGN PATENT DOCUMENTS

| | | | |
|---|---|---|---|
| CA | 982946 | * | 2/1976 |
| WO | 00/18365 | * | 4/2000 |

* cited by examiner

*Primary Examiner*—Shep K. Rose
(74) *Attorney, Agent, or Firm*—Bernard Lieberman

(57) ABSTRACT

A dentifrice composition comprising an orally acceptable vehicle having distributed therein a water hydratable film flakes having a matrix comprised of a water soluble hydroxy alkyl cellulose polymer and a starch, and having entrained therein a constituent selected from therapeutic cosmetic and decorative materials.

8 Claims, No Drawings

DENTIFRICE CONTAINING FUNCTIONAL FILM FLAKES

BACKGROUND OF THE INVENTION

1. Field of the Invention

This invention relates to a dentifrice and more particularly to a dentifrice containing rapidly water hydratable film flakes suspended in the dentifrice composition which impart to the dentifrice decorative, cosmetic and therapeutic benefits.

2. The Prior Art

Aesthetic effects have been acknowledged to play an important role in consumer acceptance of many products. In many cases ornamental effects have been used to distinguish particular products in the marketplace and identify products having particular distinct properties. In the dentifrice field, substantially clear dentifrice products such as toothpastes and gels which have incorporated therein contrasting colored flakes are known. Such flakes provide an aesthetic effect which the consumer finds pleasing and promotes the use of the dentifrice, particularly by children. Although such products have met with consumer approval, the art seeks to further improve the aesthetic effects as well as the cosmetic and therapeutic benefits of these products so as to encourage the use of dentifrices in practicing oral hygiene.

SUMMARY OF THE INVENTION

In accordance with the present invention there is provided a dentifrice having suspended therein flakes of a water hydratable film (hereinafter film flakes) comprised of a homogeneous mixture of a water soluble hydroxyalkyl cellulose polymer and starch, the film matrix having entrained therein an agent selected from therapeutic, cosmetic and decorative agents.

In one embodiment of the invention there is provided an aesthetically decorative dentifrice having distributed throughout film flakes in which a decorative colorant is entrained in the film matrix, the dentifrice vehicle being substantially clear so that the aesthetically decorative effect can be viewed by the user.

In a second embodiment, therapeutic agents such as antibacterial agents and fluoride anticaries salts, are entrained in the film flake matrix.

In a third embodiment cosmetic agents such as sweetening agents, breath freshening agents, are entrained in the film flake matrix which flavorants are rapidly released as the flakes disintegrate during toothbrushing, delivering a pleasing burst of sweetness or breath freshening flavor into the oral cavity.

The entrainment of the therapeutic and cosmetic agents in the film flake matrix suspended in the dentifrice isolates these agents from interaction with reactive ingredients present in the dentifrice so that the agents are maintained substantially separate from the reactive dentifrice ingredients during manufacture and storage while subsequently being released from the film matrix when the dentifrice containing the film flakes is topically applied to the tooth surface as by tooth brushing.

DESCRIPTION OF THE PREFERRED EMBODIMENTS

The term "substantially clear" when used in to describe the present invention shall mean translucent or transparent. The term "dentifrice" shall include toothpastes and gels.

The Film Flakes

The film flakes of the present invention are formed from a matrix comprised of hydroxyalkyl methylcellulose starch and starch film forming agents in which is entrained a colorant such a dye or pigment, a flavorant, sweetener and/or a therapeutic agent such as an antibacterial agent or a breath freshening agent. The film matrix can further comprise water, additional film forming agents, plasticizing agents, surfactants and emulsifying agents.

Preparation of Film Matrix

In preparing the film matrix according to the present invention the hydroxyalkylmethyl cellulose, a starch ingredient, a colorant, flavor, sweetener and/or therapeutic agents and other film forming ingredients are dissolved in a compatible solvent to form a film forming composition. The film forming composition is cast on a releasable carrier and dried to form a sheet of film matrix material. The carrier material must have a surface tension which allows the film solution to spread evenly across the intended carrier width without soaking to form a destructive bond between the film carrier substrates. Examples of suitable carrier materials include glass, stainless steel, Teflon and polyethylene-impregnated paper. Drying of the film may be carried out at high temperature using a drying oven, drying terminal, vacuum drier, or any other suitable drying equipment which does not adversely effect the ingredients of which the film is composed.

The film thickness ranges in size from 0.5 to 10 microns and preferably 2 to 3 microns. The dried film of the present invention is then cut or punched into shaped flakes having a particle size of 0.01 to 0.50 inches preferably 0.08 to 0.25 inches.

Additional stability can be provided to the shapes formed from the dried film, by applying to the film, before shaping into flakes, a protective barrier overcoat such as a food grade shellac or ethyl cellulose.

When the film is to be used for decorative effect, the film once formed is punched into various attractive shaped flakes such as hearts, stars, diamonds and circles. The film flakes are incorporated in the base dentifrice of the present invention at a concentration of about 0.05 to 1.0% by weight and preferably 0.1 to about 0.5% by weight.

Film Forming Agents

The major film forming agent used to prepare the film matrix of the present invention is an hydroxyalkyl cellulose such as hydroxypropyl methyl cellulose, hydroxyethylpropyl cellulose, hydroxybutyl methyl cellulose, hydroxy propyl methyl cellulose and carboxymethyl cellulose. Preferably the cellulose polymer is a low viscosity hydropropylmethyl cellulose polymer (HPMC). When HPMC is used as the film forming agent it is preferred that the HPMC have a viscosity in the range of about 1 to about 40 millipascal seconds (mPa.s) as determined as a 2% by weight aqueous solution of the HPMC at 20° C. using a Ubbelohde tube viscometer. Preferably the HPMC has a viscosity of about 3 to about 20 mPa.s at 20° C.

HPMC is available commercially from the Dow Chemical Company under the trade designation Methocel E5 LV. Methocel E5 LV is a USP grade, low viscosity HPMC having 29.1% methoxyl groups and 9% hydroxyproxyl group substitution. It is a white or off-white free-flowing dry powder. As a 2 wt. % solution in water as measured with a Ubbelohde tube viscometer it has a viscosity of 5.1 mPa.s at 20° C.

The hydroxyalkyl methyl cellulose is incorporated in the film matrix in amounts ranging from about 10 to about 60% by weight and preferably about 15 to about 40% by weight.

Cold water swellable, physically modified and pregelatenized starches are particularly useful as texture modifier to increase the stiffness of the hydroxyalkyl methyl cellulose film matrix of the present invention. In the preparation of such starch products, the granular starch is cooked in the presence of water and possibly an organic solvent at a temperature not higher than 10° C. higher than the gelatinization temperature. The obtained starch is then dried.

Pregelatinized corn starch is available commercially. A preferred starch is available under the trade designation Cerestar Polar Tex-Instant 12640 from the Cerestar Company. This Cerestar starch is a pregelaterized, stabilized and crosslinked waxy maize starch. It is readily dispersible and swellable in cold water. In its dry form, it is a white free flowing powder with an average flake size no greater than 180 micrometers and 85% of the flakes are smaller than 75 micrometers. It has a bulk density of 44 lbs/ft$^3$.

The Cerestar starch has excellent cold storage and freeze-thaw stability. It has a rapid hydration rate and can reach extremely high viscosity without cooking. It has a smooth and creamy texture similar to cook-up starches. It also has excellent paste clarity and a bland flavor.

The pregelatinized starch is present in the film matrix of the present invention in an amount ranging from about 5 to about 50% by weight and preferably about 10 to about 35% by weight.

The hydroxyalkyl cellulose to starch ratio (by weight) may vary from about 1:3 to about 4:1 and preferably about 1:1.5 to about 2.5:1.

Decorative Film Flake Ingredients

Colorants used to prepare the film flakes as well as the dentifrice into which the film flakes may be suspended, are pharmacologically and physiologically non-toxic when used in the suggested amounts. The colorants include both pigments and dyes. Pigments useful in the practice of the present invention include non-toxic, water insoluble inorganic pigments such as titanium dioxide, titanium dioxide coated mica (Timiron), chromium oxide greens, ultramarine blues and pinks and ferric oxides as well as water insoluble dye lakes prepared by extending calcium or aluminum salts of FD&C dyes on alumina such as FD&C Green #1 lake, FD&C Blue #2 lake, FD&C R&D #30 lake and FD&C # Yellow 15 lake. The pigments have a flake size in the range of 5 to 1000 microns, preferably 250 to 500 microns. Pigments are incorporated in the decorative film matrix of the present invention in an amount ranging from about 1 to about 10% by weight and preferably about 2 to about 5% by weight.

A particularly preferred class of dyes are those available from Micropowders, Inc. under the trade designation Spectra bead which are high molecular weight polyethylene powders permanently colored with dyes such as FD&C Blue #1 aluminum lake.

Dyes used in the practice of the present invention are distributed uniformly throughout the film flake matrix or the dentifrice and are desirably food color additives presently certified under the Food Drug & Cosmetic Act for use in food and ingested drugs, including dyes such as FD&C Red No. 3 (sodium salt of tetraiodofluorescein), Food Red 17, disodium salt of 6-hydroxy-5-{(2-methoxy-5-methyl-4-sulphophenyl)azo}-2-naphthalenesulfonic acid, Food Yellow 13, sodium salt of a mixture of the mono and disulphonic acids of quinophtalone or 2-(2-quinolyl)indanedione, FD&C Yellow No. 5 (sodium salt of 4-p-sulfophenylazo-1-p-sulfophenyl-5-hydroxypyrazole-3 carboxylic acid), FD&C Yellow No. 6 (sodium salt of p-sulfophenylazo-B-naphtol-6-monosulfonate), FD&C Green No. 3 (disodium salt of 4-{[4-(N-ethyl-p-sulfobenzylamino)-phenyl]-(4-hydroxy-2-sulfoniumphenyl)-methylene}-[1-(N-ethyl-N-p-sulfobenzyl)-Δ-3,5-cyclohexadienimine], FD&C Blue No. 1 (disodium salt of dibenzyldiethyl-diaminotriphenylcarbinol trisulfonic acid anhydrite), FD&C Blue No. 2(sodium salt of disulfonic acid of indigotin) and mixtures thereof in various proportions.

The concentration of the dye is present in the film matrix in an amount ranging from about 0.5 to about 5 and preferably about 1 to about 4% by weight.

The dentifrice base in which the film flakes are suspended is preferably substantially clear and contains a dye or pigment contrasting to that incorporated in the film flakes. Concentration of a contrasting dye or pigment in the dentifrice can range in an amount from about 0.05 percent to about 10 percent by weight with respect to the weight of the base dentifrice and preferably present from about 0.1 percent to about 5 percent by weight of the weight of the dentifrice base.

The film matrix of the present invention is rupturable during tooth brushing so that flavors, sweeteners as well as therapeutic agents may be maintained substantially separate from the dentifrice ingredients during manufacture and storage, while subsequently being released when the dentifrice is applied topically to tooth surfaces, the mechanical agitation created during tooth brushing effecting rupture of the film matrix whereby the entrained ingredient is released to the tooth surface.

Cosmetic Agents

Flavor agents incorporated in the film matrix of the present invention are known to the prior art, such as natural and artificial flavors. These flavorings may be chosen from synthetic flavor oils and flavoring aromatics, and/or oils, oleo resins and extracts derived from plants, leaves, flowers, fruits and so forth, and combinations thereof. Representative flavor oils include: spearmint oil, cinnamon oil, peppermint oil, clove oil, bay oil, thyme oil, cedar leaf oil, oil of nutmeg, oil of sage, and oil of bitter almonds. These flavor agents can be used individually or in admixture. Commonly used flavors include mints such as peppermint, artificial vanilla, cinnamon derivatives, and various fruit flavors, whether employed individually or in admixture. Generally, any flavoring or food additive, such as those described in Chemicals Used in Food Processing, publication 1274 by the National Academy of Sciences, pages 63–258, may be used. Generally the flavoring agent is incorporated in the film of the present invention in an amount ranging from about 1 to about 30% by weight and preferably about 15 to about 25% by weight.

Sweeteners may also be incorporated in the film matrices of the present invention include both natural and artificial sweeteners. Suitable sweetener include water soluble sweetening agents such as monosaccharides, disaccharides and plysaccharides such as xylose, ribose, glucose (dextrose), mannose, glatose, fructose (levulose), sucrose (sugar), maltose, water soluble artificial sweeteners such as the soluble saccharin salts, i.e., sodium or calcium saccharin salts, cyclamate salts dipeptide based sweeteners, such a L-aspartic acid derived sweeteners, such as L-aspartyl-L-phenylalaine methyl ester (aspartame).

In general, the effective amount of sweetener is utilized to provide the level of sweetness desired for a particular film matrix composition, will vary with the sweetener selected. This amount will normally be about 0.01% to about 2% by weight of the composition.

Therapeutic Agents

Therapeutic agents incorporated in the film flake matrix of the present invention are compounds that are reactive with dentifrice ingredients and must therefore be isolated from the dentifrice ingredients during manufacture and storage.

The therapeutic agents entrained in the film matrix maintained substantially separate from the ingredients of the base dentifrice during manufacture and storage are subsequently released into the dentifrice during tooth brushing. Entrainment of the therapeutic agent in the film matrix prevents premature leakage into the dentifrice so that in the case of therapeutic agents which are reactive ingredients, interaction with dentifrice ingredients is avoided.

For example, reaction of a cationic therapeutic agent such as cetyl pyridinium chloride or chlorhexidene with an anionic surfactant such as sodium lauryl sulfate, which surfactant is conventionally included in dentifrice compositions, inactivates the therapeutic agent thereby reducing the antibacterial efficacy of the dentifrice composition.

In the use of fluoride salts as anticavities agents, one of the methods used to achieve enhanced fluoridation known to the art (U.S. Pat. Nos. 5,045,305 and 5,145,668), is to mix, immediately before use, separate solutions containing fluoride and calcium salts. Such a procedure is a time consuming daily chore which discourages its use. Combining the calcium and fluoride salts into a single dentifrice composition will not provide an effective means for fluoridation as the presence of the calcium salt reacts with and removes bioactive soluble ionic fluoride from the dentifrice by forming insoluble and inactive calcium fluoride thereby reducing the antiocariogenic effectiveness of the fluoride dentifrice. Incorporating the calcium salt in the flakes formed from the film matrix of the present invention isolates the fluoride ion in the dentifrice from interaction with the calcium salt until the film matrix disintegrates during tooth brushing.

Typically, in the case of calcium salts, these salts are present in the film flake matrix in an amount up to about 30% by weight, based on the weight of the film matrix, and preferably in the amount of about 18% to 22%.

In addition to fluoride or calcium salts, there may also be included in the film flake matrix anticalculus agents such as pyrophosphate salts including dialkali or tetraalkali metal pyrophosphate salts such as $Na_4P_2O_7$, $K_4P_2O_7$, $Na_2K_2P_2O_7$, $Na_2H_2P_2O_7$ and $K_2H_2P_2O_7$, long chain polyphosphates such as sodium hexametaphosphate and cyclic phosphates such as sodium trimetaphosphate which are included in the film matrix at a concentration of about 15 to 20% by weight.

Other active agents which may be incorporated it he film matrix of this invention include antibacterial agents such as Triclosan, breath freshening agents such as zinc gluconate, zinc citrate and/or alpha ionone, desensitizers such as potassium nitrate, vitamins such as pantheon, retinyl palmitate, tocopherol acetate, herbs such as chamomilla recutita, mentha piperita, salvia officinalis, commiphora myrrha, whitening agents such as hydrogen peroxide and urea peroxide, high cleaning silica, preservatives, silicones, chlorophyll compounds.

The active agents are incorporated in the film matrix of the present invention at a concentration of about 0.1 to about 2.0% by weight and preferably about 0.15 to about 5% by weight. The present invention is illustrated by the following examples.

Base Dentifrice Composition

In the preparation of the base dentifrice in accordance with the present invention there is utilized an orally acceptable vehicle, including a water-phase with humectant which is preferably glycerine or sorbitol or an alkylene glycol such as polyethylene glycol or propylene glycol, wherein the water is present typically in amount of about 5 to about 10% by weight and the glycerine, sorbitol and/or the alkylene glycol ingredients typically total about 30 to about 80% by weight of the dentifrice, more typically about 50 to about 70% by weight.

The base dentifrice also contains an inorganic or a natural or synthetic thickener or gelling agent in proportions of about 0.10 to about 5% by weight, preferably about 0.2 to about 1% by weight. These proportions of thickeners in the dentifrice compositions of the present invention in which the film flakes of the present invention are suspended are sufficient to form an extrudable, shape-retaining product which can be squeezed from a tube onto a toothbrush and will not fall between the bristles of the brush but rather, will substantially maintain its shape thereon. Suitable thickeners or gelling agents useful in the practice of the present invention include inorganic thickening silicas such as amorphous silicas available from Huber Corporation under the trade designation Zeodent 165, Irish moss, iota-carrageenan, gum tragacanth, and polyvinylpyrrolidone.

Polishing agents such as silica, calcined alumina, sodium bicarbonate, calcium carbonate, dicalcium phosphate and calcium pyrophosphate may be included in the base dentifrice compositions used in the practice of the present invention. Visually clear dentifrice compositions are obtained by using polishing agents such as collodial silica, such as those sold under the trade designation Zeodent 115 available from the Huber Corporation or alkali metal aluminosilicate complexes (that is, silica containing alumina combined in its matrix) which have refractive indices close to the refractive indices of gelling agent-liquid (including water and/or humectant) systems used in dentifrice compositions.

The polishing agent is generally present in the base dentifrice composition in weight concentrations of about 3% to about 50% by weight.

Surfactants are used in the base dentifrice compositions of the present invention to achieve increased prophylactic action and render the instant compositions more cosmetically acceptable. Suitable examples of surfactants include water-soluble salts of higher fatty acid monoglyceride monosulfates, such as the sodium salt of the monsulfated monoglyceride of hydrogenated coconut oil fatty acids, cocamidopropyl betaine, higher alkyl sulfates such as sodium lauryl sulfate, alkyl aryl sulfonates such as sodium dodecyl benzene sulfonate, higher alkyl sulfoacetates, sodium lauryl sulfoacetate, higher fatty acid esters of 1,2-dihydroxy propane sulfonate, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosine, and the sodium, potassium, and ethanolamine salts of N-lauroyl, N-myristoyl, or N-palmitoyl sarcosine.

The anionic surfactants are typically present in the dentifrice compositions of the present invention in an amount of about 0.3to about 5% by weight, preferably about 0.5 to about 2.0% by weight.

To prepare the dentifrice base of the present invention, water, humectants, e.g. glycerin, sorbitol polyethylene glycol are dispersed in a conventional mixer until the mixture becomes a homogeneous gel phase. Into the gel phase are added the polishing agent. These ingredients are mixed until a homogeneous phase is obtained. Thereafter the thickener, any flavor and surfactant ingredients are added and the ingredients mixed at high speed until vacuum of about 20 to 100 mmHg. The shaped film flakes are added to the dentifrice constituents as a last step, so as to minimize the shear to which the dentifrice ingredients are subjected to during the prior mixing steps.

EXAMPLE I

Silver colored film flakes were prepared by using the ingredients listed in Table I below. In preparing the film, the HMPC polymer Methocel E5LV having a viscosity of 5.1 mPa.s (2% aqueous solution) was added to deionized water at 23° C., and the solution stirred for 5 minutes. To this solution was added the pregelatized starch Cerestar Polar Tex Instant 12640 and stirred vigorously for about one hour until the starch was completely dispersed and a homogeneous mixture was formed. To this mixture was added the titanium coated mica and mixed for 10 minutes after which the sodium lauryl sulfate surfactant was added and mixed for an additional 15 minutes. Thereafter spearmint flavor was thoroughly mixed for an additional 40 minutes to form a slurry emulsion. The weight ratio of HPMC to Starch was 2:1. The emulsion was then cast on a polyethylene coated paper at 25° C. and dried at 110° C. to form a solid thin film having a thickness of 2.5 microns. Star shaped flakes punched from the dried film had a particle size of 0.25 inches.

A transparent green colored base dentifrice composition having the ingredients listed in Table II was prepared, wherein a vehicle solution of the sorbitol and water was made and subjected to 28–30 lbs. applied vacuum and a mixture of saccharin sodium fluoride and was added thereto. Subsequently, a green dye was blended with the vehicle. The mixture was degassed at 28–30 lbs. applied vacuum over a 5 minute period. Then Zeodent 115 silica abrasive and Zeodent 165, an amorphous silica thickening agent and sodium lauryl sulfate (SLS) were added after preliminary degassing. The ingredients were mixed. After about 5 minutes mixing, with application of vacuum, the dentifrice preparation was considered to be complete and thereafter 0.3% by weight of the star shaped film flakes were suspended in the dentifrice.

After packaging, the dentifrice product was squeezed from a tube and was extruded as a distinctive green, aesthetically pleasing ribbon product having suspended therein clearly visible star shaped silver colored flakes extending throughout the extruded product.

TABLE I

SILVER FILM MATRIX

| Ingredients | Wt. % |
|---|---|
| Starch | 21.0 |
| HPMC | 40.0 |
| Glycerin | 5.0 |
| Vegetable oil | 3.0 |
| Tween 80 | 1.0 |
| SLS | 1.0 |
| Sodium saccharin | 0.3 |
| Titanium coated mica | 3.8 |
| Flavor | 24.6 |
| Zinc gluconate | 0.3 |
| Total | 100 |

TABLE II

GREEN BASE DENTIFRICE

| Ingredients | Wt. % |
|---|---|
| PEG 600 | 3.0 |
| Sodium carboxymethyl cellulose | 0.55 |
| Sorbitol | 74.0 |
| Purified water | 6.357 |
| Sodium fluoride | 0.243 |
| Tetrasodium pyrophosphate | 0.50 |
| Sodium saccharine | 0.30 |
| Zeodent 115 | 4.0 |
| Zeodent 165 | 8.8 |
| Sodium lauryl sulfate | 1.2 |
| Flavor | 1.0 |
| FD&C Green (2% soln.) | 0.05 |
| Total | 100 |

EXAMPLE II

A second film flake was prepared following the procedure of Example I. The ingredients of the film matrix are listed in Table III below.

TABLE III

RED FILM

| Ingredients | Wt. % |
|---|---|
| HPMC | 48.0 |
| Cornstarch | 12.0 |
| Propylene glycol | 2.0 |
| Tween 80 | 2.0 |
| Vegetable oil | 4.0 |
| Flavor | 24.0 |
| FD&C #33 | 4.0 |
| Titanium oxide coated mica | 4.0 |
| Total | 100 |

The thickness of the film was 3.0 microns. Thereafter 0.2% by weight of heart shaped flakes having a particle size of 0.125 inches were die cut from the film. Shellac (100% non-bleached) was applied to the film before the heart shapes were die cut from the matrix. The heart shaped flakes were then incorporated into the dentifrice base of Table II as the last step, so as to minimize the shear to which they are subjected to during mixing.

After packaging, the dentifrice product was squeezed from a tube and was extruded as a distinctive blue, aesthetically pleasing product having suspended therein clearly visible heart shaped red colored flakes extending randomly throughout the extruded product.

EXAMPLE III

Film flakes suitable for the delivery of a flavor burst having a high flavor concentration (23.75wt. %) was prepared following the procedure of Example I, the ingredients of which are listed in Table IV. Flakes in the shape of circles formed from the film were suspended in a base dentifrice of type disclosed in Table II. When brushed on teeth the dentifrice emitted a burst of flavor as the brushing caused the mechanical rupture of the film with the immediate release of its flavor constituent.

TABLE IV

| Ingredients | Wt. % |
| --- | --- |
| HPMC | 48.0 |
| Cornstarch | 12.0 |
| Tween 80 | 2.0 |
| Propylene glycol | 2.0 |
| Canola oil | 4.0 |
| Flavor | 23.75 |
| Titanium coated mica | 8.0 |
| Sodium fluoride | 0.243 |
| Total | 100 |

EXAMPLE IV

A film of 2.5 microns thickness containing a high concentration of calcium acetate (21.4% by weight) was prepared following the procedure of Example I having the ingredients listed in Table V below:

TABLE V

| Ingredients | Wt. % |
| --- | --- |
| HPMC | 43.0 |
| Calcium acetate | 21.4 |
| Tween 80 | 1.8 |
| Propylene glycol | 1.8 |
| Canola oil | 3.5 |
| Flavor | 21.4 |
| Titanium coated mica | 7.1 |
| Total | 100 |

0.3% by weight film flakes of 0.25 inch particle size of Table V were suspended in a commercial fluoride toothpaste containing 1100 parts per million (ppm) fluoride ion. The toothpaste containing the film flakes designated "Paste A", was then aged at 120° F. for 2 to 8 weeks and analyzed for fluoride content at weekly intervals. For purposes of comparison, the same toothpaste to which the film flakes had not been incorporated designated "Paste B", was also analyzed for fluoride levels during the same two week interval.

The presence of fluoride ion in the dentifrice at each week interval was determined by separating the base from the flakes first then analyzing the base for the presence of fluoride using F⁻ ion selective electrodes. The results of these assays are recorded in Table VI below.

The fluoride assays of the two toothpastes are recorded in Table VI below.

TABLE VI

| Weeks Paste | 1 (ppmF-) | 2 (ppmF-) | 3 (ppmF-) | 4 (ppmF-) | 8 (ppmF-) |
| --- | --- | --- | --- | --- | --- |
| A | 935 | 962 | 900 | 943 | 899 |
| B | 1016 | 1042 | 986 | 1036 | 1040 |

The results recorded in Table VI show a minimal loss of fluoride ion over the 8 week assay period in Paste A containing film entrained calcium acetate as compared to Paste B which did not contain any calcium salt. When brushed on teeth of the film suspended in the dentifrice will rapidly disintegrate whereby calcium ion will be released to interact with the fluoride ion to enhance the anticaries efficacy of the fluoride ion on the teeth being brushed.

EXAMPLE VI

Cetyl pyridinium chloride (CPC) is incompatible with sodium lauryl sulfate (SLS) a surfactant widely used in dentifrice compositions. Because of this incompatibility CPC has not found application in most dentifrice formulations. In Table VII below there is listed the ingredients of a film matrix in which CPC is entrained. The film when suspended in a SLS containing dentifrice will not react with the SLS present in the dentifrice. The CPC will be released during tooth brushing without being inactivated by the presence of SLS in the toothpaste base.

TABLE VII

| Ingredients | Wt. % |
| --- | --- |
| HPMC | 48.0 |
| CPC | 12.0 |
| Tween 80 | 2.0 |
| Propylene glycol | 2.0 |
| Canola oil | 4.0 |
| Flavor | 24.0 |
| Titanium coated mica | 8.0 |
| Total | 100 |

What is claimed is:

1. A dentifrice composition comprising an orally acceptable vehicle which a transparent clear gel dentifrice comprising a polishing agent, surfactant, a thickening or gelling agent and humectant in an aqueous vehicle, said clear gel dentifrice containing an aesthetically shaped decorative film flake matrix comprising (A) titanium coated mica, and admixtures of (A) with (B) polyethylene powder colored with F. D & C dyes; and/or (C) F. D. & C certified food color additive colorants, dyes, pigments, and lakes, and (D) mixtures of (A) (B) and (C), said decorative film flake matrix being aesthetically shaped to appeal to consumers and to their children when visible in said transparent substantially clear gel dentifrice, said decorative film flake matrix being formed from a dried film matrix of F. D & C certified food color additive colorant, a water soluble hydroxyalkyl cellulose polymer and a starch, said dried film then being cut or punched into various attractive shapes, including hearts, stars, diamonds, and circles, said shaped flakes having a particle size of 0.01 to 0.50 inches.

2. A dentifrice according to claim 1 wherein the film flake matrix has further entrained therein a cosmetic constituent.

3. A dentifrice according to claim 1 wherein the film flake matrix has further entrained therein a therapeutic constituent.

4. The dentifrice according to claim 1 in which the film flake matrix comprises from about 0.05 to about 1.0% by weight of the dentifrice.

5. The dentifrice of claim 3 wherein the therapeutic constituent further entrained in the film flake matrix is an antibacterial agent.

6. The dentifrice of claim 3 wherein the therapeutic constituent further entrained in the film flake matrix is a calcium or fluoride salt.

7. The dentifrice of claim 4 wherein the cosmetic constituent further entrained in the film flake matrix is a flavorant.

8. The dentifrice of claim 7 wherein the flavorant is present in the film flake matrix at a concentration of about 15 to about 25% by weight.

* * * * *